United States Patent
Rowen

(10) Patent No.: US 9,351,902 B2
(45) Date of Patent: May 31, 2016

(54) METHOD AND DEVICE FOR SCAR MANAGEMENT

(71) Applicant: Elan Pharma International Ltd., Dublin (IE)

(72) Inventor: Jessica Rowen, Guilford, CT (US)

(73) Assignee: Elan Pharma International Ltd., Dublin (IE)

( * ) Notice: Subject to any disclaimer, the term of this patent is extended or adjusted under 35 U.S.C. 154(b) by 0 days.

(21) Appl. No.: 14/464,443

(22) Filed: Aug. 20, 2014

(65) Prior Publication Data

US 2014/0358051 A1 Dec. 4, 2014

Related U.S. Application Data

(63) Continuation of application No. 13/624,605, filed on Sep. 21, 2012, now abandoned.

(60) Provisional application No. 61/567,426, filed on Dec. 6, 2011.

(51) Int. Cl.
*A61H 15/00* (2006.01)
*A61M 35/00* (2006.01)
(Continued)

(52) U.S. Cl.
CPC .............. *A61H 15/02* (2013.01); *A45D 34/041* (2013.01); *A61H 15/0092* (2013.01);
(Continued)

(58) Field of Classification Search
CPC .............. A61H 15/0092; A61H 15/02; A61H 2015/0064; A61H 2201/105; A61H 23/00; A61K 31/695; A61K 8/25; A61M 35/00; A61M 35/003; A61D 34/041
See application file for complete search history.

(56) References Cited

U.S. PATENT DOCUMENTS

| 1,947,042 A | 2/1934 | Glennan |
| 3,542,016 A | 11/1970 | Zimmer |

(Continued)

FOREIGN PATENT DOCUMENTS

WO 0123011 A1 4/2001

OTHER PUBLICATIONS

Klykken et al. "Silicone Film-Forming Technologies for Health Care Applications" (retrieved from http://www.dowcorning.com/content/publishedlit/52-1068-01.pdf by the USPTO on May 12, 2014, publically available from at least Jan. 14, 2005, as confirmed by https://web.archive.org/web/*/http://www.dowcorning.com/content/publishedlit/52-1068-01.pdf).*

(Continued)

*Primary Examiner* — Tatyana Zalukaeva
*Assistant Examiner* — Benjamin Klein
(74) *Attorney, Agent, or Firm* — Honigman Miller Schwartz and Cohn LLP; Noel E. Day; Jonathan P. O'Brien

(57) ABSTRACT

A device for scar management includes an applicator head including a recess having a rotating means therein, a reservoir containing a silicone composition fluidly connected to the applicator head, and a metering valve fluidly connected to the reservoir. The composition has viscosity of 3,000 to 8,000 cps, and consists of a mixture of cyclopentasiloxane, dimethiconol, dimethicone, and dimethicone/vinyl dimethicone crosspolymer. A metered dose of the silicone composition is delivered from the reservoir to the applicator head upon the application of external pressure to the metering valve. The invention also relates to a method for scar management using such device by identifying a target skin area having a wound or scar, contacting the outward surface of the applicator head to the target skin area, massaging the rotating means of the applicator head on the target skin area, and applying the silicone composition to the target skin area via the rotating means.

11 Claims, 3 Drawing Sheets

(51) Int. Cl.
*A61H 15/02* (2006.01)
*A45D 34/04* (2006.01)
*A61H 23/00* (2006.01)
*A61K 31/695* (2006.01)
*A61K 31/80* (2006.01)

(52) U.S. Cl.
CPC ............. *A61H 23/00* (2013.01); *A61K 31/695* (2013.01); *A61K 31/80* (2013.01); *A61M 35/003* (2013.01); *A61H 2015/0064* (2013.01); *A61H 2201/105* (2013.01)

(56) References Cited

U.S. PATENT DOCUMENTS

| | | | | |
|---|---|---|---|---|
| 5,131,384 | A * | 7/1992 | Obagi | 601/131 |
| 5,795,575 | A | 8/1998 | Bombardelli et al. | |
| 7,205,012 | B1 | 4/2007 | Hill | |
| 7,241,451 | B1 * | 7/2007 | Edell et al. | 424/401 |
| 7,482,314 | B2 | 1/2009 | Grimes et al. | |
| 2004/0234474 | A1 | 11/2004 | Berlat | |
| 2005/0054991 | A1 * | 3/2005 | Tobyn et al. | 604/290 |
| 2005/0143345 | A1 | 6/2005 | Hardy | |
| 2008/0154161 | A1 | 6/2008 | Abbott | |
| 2009/0143333 | A1 * | 6/2009 | Palefsky et al. | 514/63 |
| 2009/0198159 | A1 | 8/2009 | Linzell | |
| 2011/0020264 | A1 | 1/2011 | Studin | |

OTHER PUBLICATIONS

Berman, et al.; "A Review of the Biological Effects, Clinical Efficacy and Safety of Silicone Elastomer Sheeting for Hypertrophic and Keloid Scar Treatment and Management"; Dermatological Surgery 33:Nov. 11, 2007, pp. 1291-1303.

Mustoe, et al.; "International Clinical Recommendations on Scar Management"; American Society of Plastic Surgeons; 2002; pp. 560-571.

International Search Report and Written Opinion of the International Searching Authority Application No. PCT/US2012/066026 Completed: Jan. 3, 2013; Mailing Date: Jan. 29, 2013 8 pages.

Klykken et al. "Silicone Film-Forming Technologies for Health Care Applications" (retrieved from http://www.dowcorning.com/content/publishedlit/52-1068-01.pdf by the US PTO on May 12, 2014, publically available from at least Jan. 14, 2005, as confirmed by https://web.archive.org/web/*/http://www.dowcorning.com/content/publishedlit/52-1068-01.pdf).

* cited by examiner

METHOD AND DEVICE FOR SCAR MANAGEMENT

FIELD OF THE INVENTION

The present invention relates to a method for managing scars, namely treating existing scars or preventing the formation of various types of scars. The invention also relates to a device suitable for use in the method of the invention.

BACKGROUND OF THE INVENTION

Hypertrophic and keloid scars are abnormal scars that develop from the biological process of wound repair in the skin. Hypertrophic scars and keloids are raised, thickened, discolored scars that are typically stiffer than the surrounding skin. Both types of scars are often tender, itchy, and even painful.

Keloid scars are the result of an overly aggressive healing process. These scars extend beyond the original injury. Over time, a keloid scar may affect mobility. Left untreated, keloids can continue to grow quite large. Hypertrophic scars are raised and red scars that are similar to keloids, but do not breach the boundaries of the injury site.

Most people desire to minimize the appearance of such scars. Several treatments and preventative methods exist, including steroid injections and surgery.

Silicone is a noninvasive treatment that has demonstrated significant improvement in the overall look and texture of scars, including improvement in scar elasticity in those prone to abnormal scarring. Various prescription and over-the-counter products are available, including Applicant's own ScarAway™ silicone scar sheets. The differences among these products generally lie in their physical characteristics. For instance, sheets are provided with and without adhesive backing. Other products include polyurethane foam, pressure garments, splints, silicone gels, ointment sprays to form a thin coat of silicone over skin surface, and liquid strips enhanced with various vitamins or steroids.

Silicone gel sheeting, which is standard of care for plastic surgeons, has been widely used since the 1980s. There are several hypotheses that try to explain its efficacy in treating hypertrophic and keloid scars. Possible mechanisms include increased temperature, hydration caused by occlusion of the underlying skin, increased oxygen tension, direct action of the silicone oil, and polarization of the scar tissue caused by the negative static electric charge generated by movement of the silicone. See Berman et al., *A Review of the Biological Effects, Clinical Efficacy and Safety of Silicone Elastomer Sheeting for Hypertrophic and Keloid Scar Treatment and Management*, Dermatological Surgery 33:11 November 2007, pp. 1291-1303. A drawback of silicone sheeting is that it must be worn for 12 hours per day for 2 to 3 months to be effective.

Another known method of scar treatment is pressure therapy, which is particularly useful for hypertrophic burn scars. It is recommended that pressure be maintained between 24 and 30 mm Hg for 6 to 12 months for this therapy to be effective. More costly or invasive techniques include radiotherapy, laser therapy and cryotherapy.

Massage is a physical management option for scar treatment often used by physical therapists, occupational therapists and other allied health care professionals, but has not been clinically proven by long-term studies. Massage is often combined with other scar management techniques to treat burn scars.

U.S. Pat. No. 7,241,451 to Edell et al. discloses a topical cream containing silicone and sunscreen that is applied to scars. Silicone is only 1.0 to 7.0% of the composition. The cream is to be applied twice daily and massaged into the scar area for two to three minutes to aid in breaking up collagen or scar tissue, reducing the appearance of scar tissue. However, the massage method is not described and the amount of cream applied is not controlled.

Because of the pain, itching and unpleasing appearance associated with hypertrophic and keloid scars, there is a desire to have new and improved techniques to treat and prevent the formation of these scars. It also desirable for these techniques to be affordable, available for over-the-counter purchase, easy to use and involve minimal time commitment.

SUMMARY OF THE INVENTION

The present invention aims to improve upon the deficiencies in prior scar treatments. Particularly, it is an object of the present invention to provide effective, yet convenient to use techniques to prevent or reduce scarring of healed wounds or to improve the size and appearance of formed scars, particularly keloid and hypertrophic scars.

These objectives are achieved through a device for scar management comprising a massaging applicator head and a reservoir containing a silicone composition that is applied to the skin through a conduit from the reservoir to a rotating means located within a recess in the applicator head.

In preferred embodiments, the rotating means is a spherical ball seated in a recess within the head and having a portion of the ball projecting outwardly through the recess aperture and freely rotatable within the recess.

In some embodiments there are a plurality of recesses and rotating means.

In certain embodiments, the composition comprises 25-100% by weight of silicones in the composition. In certain of these embodiments, the composition comprises 50-100% by weight of silicones. In yet certain of these embodiments, the composition comprises 75-100% by weight of silicones. In preferred embodiments, the composition comprises 95-100% by weight of silicones. In a particularly preferred embodiment, the composition comprises 100% silicones.

In some embodiments the composition further comprises sun protection agents.

In some embodiments, the device further comprises a metering valve in fluid communication with the reservoir for dispensing a fixed amount of silicone composition from the reservoir to the applicator head when pressure is applied.

In certain embodiments, the metering valve is in communication with a metering dome that delivers the metered dose of composition when pressure is applied then released to a metering dome. In other embodiments, the metering chamber dispenses through a twist and click mechanism.

In some of these embodiments, the dispensing meter delivers 0.01-5.0 mL of the silicone composition. In some of these embodiments the dispensing meter delivers 0.02-2.5 mL of the silicone composition. Preferably, the dispensing meter delivers 0.03-1.0 mL of the silicone composition.

In some embodiments, the device further comprises vibrating means.

The device is used in the inventive method, which employs the synergistic combination of massage and silicone to treat and prevent the formation of scars. The inventive method comprises providing the above described silicone containing applicator device, identifying a target area of skin having a wound or scar, contacting the outward surface of the applicator head to the target skin area, massaging the rotating means of the on the target skin area, and applying the silicone composition to the target area via the rotating means.

In some embodiments of the inventive method, the massaging is continued for 10 seconds to 5 minutes. In some of these embodiments, the massaging is continued for 30 seconds to 3 minutes. In yet some of these embodiments, the massaging is continued for 1 to 2 minutes.

In certain embodiments of the inventive method, before the rotating means is massaged into the target area, a fixed amount of silicone composition is delivered to the applicator head. In some of these embodiments, the dispensing meter delivers 0.01-5.0 mL of the silicone composition. In some of these embodiments the dispensing meter delivers 0.02-2.5 mL of the silicone composition. Preferably, the dispensing meter delivers 0.03-1 mL of the silicone composition.

In other embodiments, the method is performed at least once a day for 0-12 weeks. In certain of these embodiments, the method is performed twice daily for 8-12 weeks.

In certain embodiments, the method is performed at least once a day for 0-6 months. In certain of these embodiments, the method is performed twice daily for 0-6 months. In yet certain of these embodiments, the method is performed twice daily for 3-6 months.

In yet other embodiments, the method is performed at least once a day for up to 18 months.

DETAILED DESCRIPTION OF THE INVENTION

Figure 1:
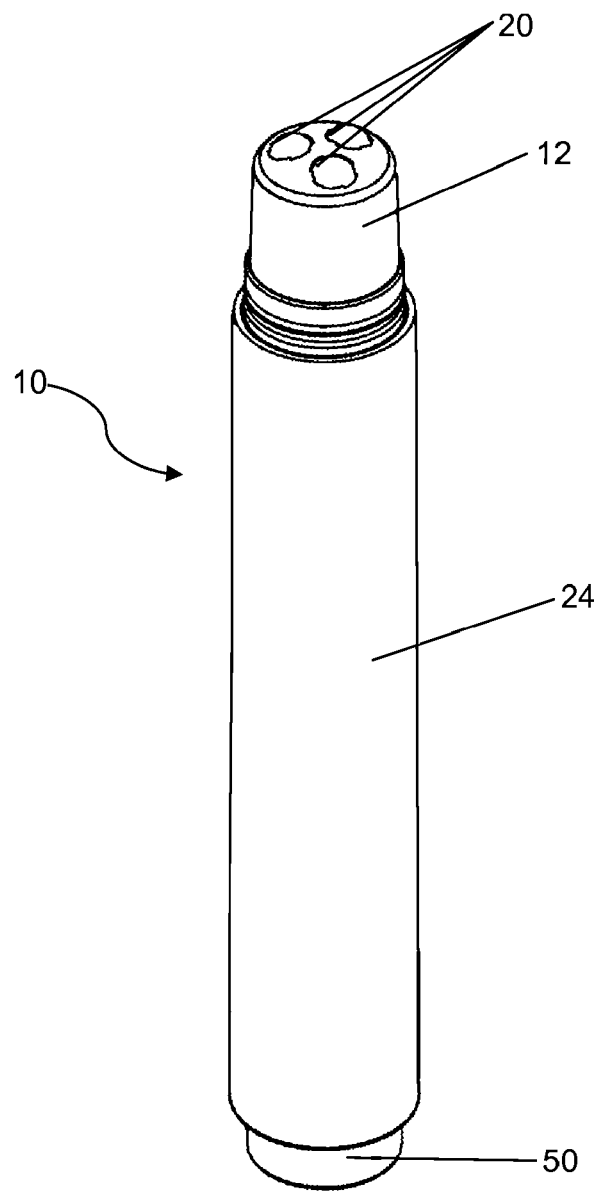
FIG. 1 is a perspective view of a device of the present invention having an applicator head with three spherical rotating means.
Figure 2:
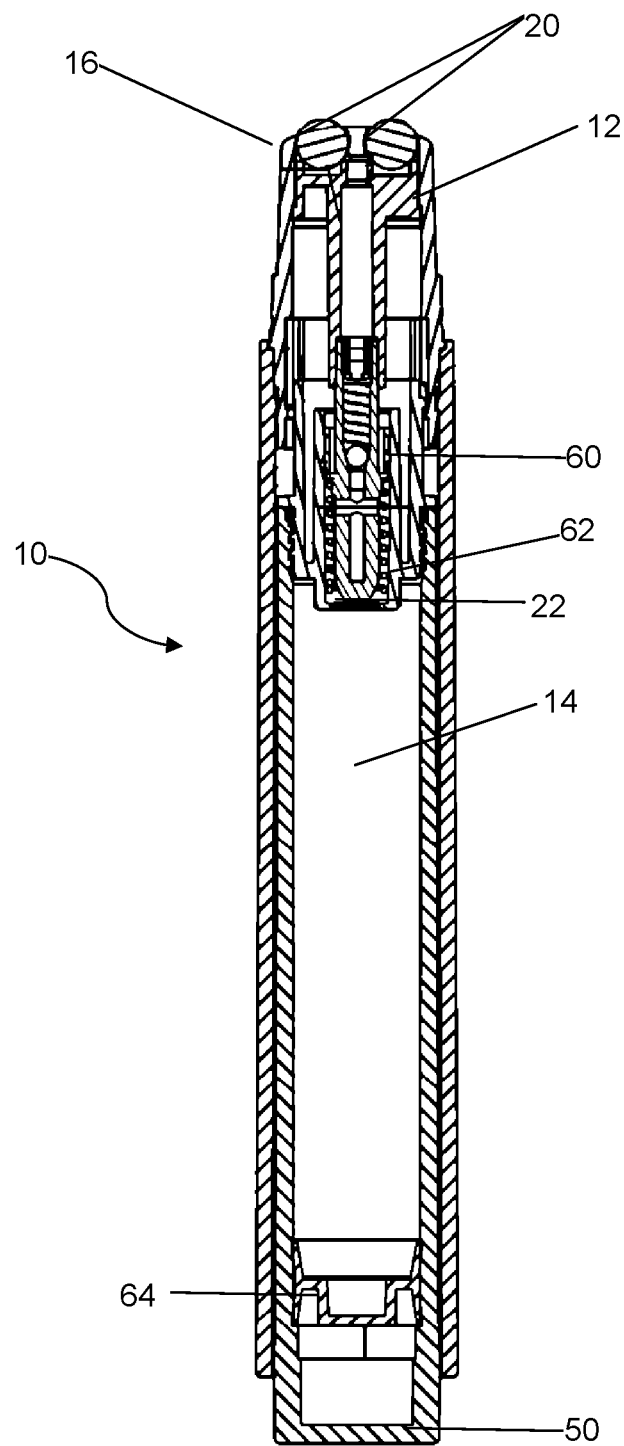
FIG. 2 is a cross-section of the device of FIG. 1.

Turning now to the drawings, FIGS. 1 and 2 shows the scar management device (10) of the present invention having an applicator head (12) with three spherical rotating means (20) that are fluidly connected to a body (24) having a reservoir (14) containing a silicone composition. The reservoir (14) is also fluidly connected to a dispensing button (50). A fixed amount of the silicone composition is delivered to the rotating means (20) when pressure is applied then released to the button (50).

FIG. 2 shows the applicator head (12) also comprising a recess (16) in the applicator head.

Preferably, the body (24) and head (12) of the device (10) are formed primarily of polypropylene, with stainless steel rotating means (20). Other materials are envisioned. The device (10) is not limited by the material forming the components.

FIG. 2 shows a dispensing valve (60), which is used to supply the silicone composition from the reservoir (14) though a conduit (22) to the rotating means (20).

The rotating means may be of any shape. In preferred embodiments, the rotating means (20) is a spherical ball seated in the recess (16) within the applicator head (12). A portion of the ball (20) projects outwardly and is freely rotatable within the recess (16). The spherical shape is particularly preferred because it provides a smooth and gentle application of silicone composition to the skin.

The device (10) contains at least one rotating means (20) in the applicator head (12). Preferably, the device (10) comprises a plurality of recesses (16) and rotating means (20).

Most preferably, the device (10) comprises three recesses (16) and three spherical ball rotating means (20).

In certain embodiments, the rotating means may have a textured surface.

The composition may comprise 25-100% by weight of silicones. In certain embodiments, the composition comprises 50-100% by weight of silicones. In other embodiments, the composition comprises 75-100% by weight of silicones. In preferred embodiments, the composition comprises 95-100% by weight of silicones. In another preferred embodiment, the composition comprises 100% by weight of a mixture of various silicones.

The composition may comprise silicones selected from the group consisting of cyclopentasiloxane, dimethiconol, dimethicone, dimethicone/vinyl dimethicone crosspolymer, cetyl dimethicone, polysiloxanes, and polydimethylsiloxane, or mixtures thereof.

A particularly preferred composition comprises 95-100% by weight of a mixture of cyclopentasiloxane, dimethiconol, dimethicone and dimethicone/vinyl dimethicone crosspolymer.

The composition may further comprise vitamins, minerals, peptides, hyaluronic acid, enzymes, sun protection agents, fruit, flower or herbal extracts, e.g., aloe (*barbadensis* leaf extract), chamomile (rectita flower extract), licorice (*glycyrrhiza glabra* root extract), thickeners, filming agents, drying agents, e.g., silica, magnesium silicate, fragrance, color, petroleum, moisturizers, and/or stabilizers. The sun protection agent may be one or more of titanium dioxide, zinc oxide, padimate O, phenylbenzimidazole sulfonic acid, cinoxate, dioxybenzone, oxybenzone, homosalate, menthyl anthranilate, octocrylene, octyl methoxycinnamate, octyl salicylate, sulisobenzone, trolamine salicylate, avobenzone, ecamsule and bisoctrizole. Preferred compositions comprise a base including petroleum, moisturizers and stabilizers.

The composition may have a viscosity in the range of 3,000-15,000 cps. Some compositions have a viscosity of 3,000 to 8,000 cps. Preferably, the silicone composition has a viscosity of 5,000 to 10,000 cps. The viscosity of the composition is important because a composition that is too viscous will not properly flow through the conduit (22). A composition that has low viscosity will not consistently dispense the predetermined dose, or will run off the skin, which is not desired. Compositions having a viscosity of 15,000 to 20,000 cps were found to be too viscous for consistent dispensing in the methods of the invention.

The composition may be a lotion, cream, gel or serum. Preferably, the composition is a serum.

Looking at FIG. 2, the dispensing meter (10) is in fluid communication with the reservoir (14) for delivering a fixed amount of silicone composition from the reservoir (14) to the applicator head (12). The dispensing valve (60) comprises a metering chamber (62) for delivering the fixed amount of silicone composition when pressure is applied then released to a metering dome (64).

The device is not limited to the dispensing valve (60) shown. For instance, the dispensing valve (60) may also deliver the fixed amount of silicone composition by a twist and click mechanism.

The amount of silicone composition delivered by the device is about 0.01-5.0 mL. Preferably, the fixed amount is 0.02-2.5 mL of the silicone composition. Most preferably, the fixed amount is 0.03-1 mL of the silicone composition. Exemplary designs deliver about 0.05 mL silicone composition per metered dose.

The device may also comprise vibrating means (not shown). Preferably the vibrating means can be activated by the user so that the user has the option to deliver silicone composition to the skin and massage the composition into the skin with or without use of vibration.

Figure 3:
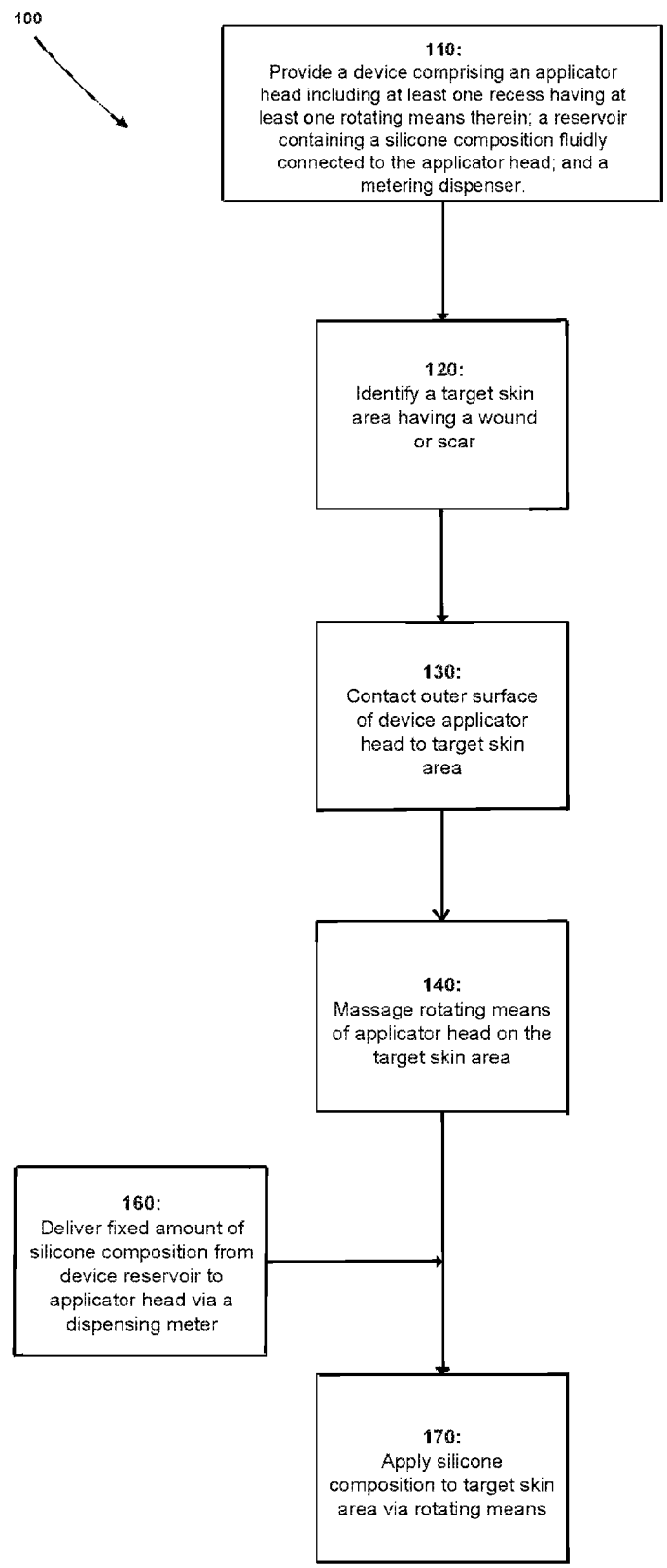
FIG. 3 is a flow diagram showing an embodiment of the inventive method.

Turning now to FIG. 3, an embodiment of the inventive method is shown. The method (100) comprises providing the above described scar management device (110), identifying a target skin area having a wound or scar, (120) contacting the outward surface of the applicator head to the target skin area (130), massaging the rotating means of the applicator head on the target skin area (140), and applying the silicone composition to the target area via the rotating means (150).

The massaging step (140) may be continued for 10 seconds to 5 minutes. In some of these embodiments, the massaging (140) is continued for 30 seconds to 3 minutes. Preferably, the massaging (140) is continued for 1 to 2 minutes.

In certain preferred embodiments the method comprises delivering a fixed amount of silicone composition (160) from the reservoir to the applicator head via a dispensing valve before the rotating means is massaged into the target skin area (140). In some of these embodiments, the fixed amount is 0.01-5.0 mL of the silicone composition. In some of these embodiments, the fixed amount is 0.02-2.5 mL of the silicone composition. Preferably, the fixed amount is 0.03-1.0 mL of the silicone composition.

Treatment duration will vary from person to person and from scar to scar depending on many factors. In some embodiments, the method is performed at least once a day for 1 day to 6 months. In other embodiments, the method is performed at least once a day for up to 12 weeks. In yet other embodiments, the method is performed at least once a day for up to 18 months. The recommended duration of treatment is 8-12 weeks for a new scar, and 3-6 months for an existing scar or until the scar stops responding or desired results are achieved. To protect a new scar the method may be practiced with a composition comprising SPF for 18 months or more as recommended by a medical professional. Best results are achieved for treatment or protection when scars treated are twice daily.

While the invention has been specifically described in connection with certain specific embodiments thereof, it is to be understood that this is by way of illustration and not of limitation and that various changes and modifications in form and details can be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. A device for scar management comprising:
   an applicator head including three recesses each having a rotating ball therein;
   a reservoir having a contents consisting of a silicone composition fluidly connected to the applicator head, said composition having a viscosity of 3,000 to 8,000 cps, and consisting of a mixture of cyclopentasiloxane, dimethiconol, dimethicone, and dimethicone/vinyl dimethicone crosspolymer; and
   a metering valve fluidly connected to the reservoir, wherein a metered dose of the silicone composition having a volume of 0.03 to 1.0 mL is delivered from the reservoir to the applicator head upon the application of external pressure to the metering valve.

2. The device of claim 1, wherein the ball is spherical.

3. The device of claim 1, wherein the silicone composition further consists of a sun protection agent.

4. The device of claim 1, wherein the metered dose of the silicone composition has a volume of 0.05 mL.

5. A method for scar management comprising:
   providing a device having an applicator head including three recesses having three rotating balls therein, a reservoir having a contents consisting of a silicone composition fluidly connected to the applicator head, said composition having a viscosity of 3,000 to 8,000 cps;
   identifying a target skin area having a wound or scar;
   contacting the outward surface of the device applicator head to the target skin area;
   dispensing a fixed amount of the silicone composition having a volume in the range of 0.03 to 1.0 mL from the reservoir to the applicator head;
   massaging the rotating ball of the applicator head on the target skin area; and applying the fixed amount of silicone composition to the target skin area via the rotating ball;
   wherein the silicone composition consists of a mixture of cyclopentasiloxane, dimethiconol, dimethicone, and dimethicone/vinyl dimethicone crosspolymer.

6. The method of claim 5, wherein the massaging is continued for 10 seconds to 5 minutes.

7. The method of claim 5, wherein said method is performed twice daily.

8. The method of claim 5, for treatment of a new scar, wherein said method is performed at least once a day for up to 12 weeks.

9. The method of claim 5, for treatment of an existing scar, wherein said method is performed at least once a day for up to 6 months.

10. The method of claim 5, for protecting a new scar, wherein said method is performed at least once a day for up to 18 months.

11. The method of claim 5, wherein 0.05 mL of the silicone composition is dispensed.

* * * * *